United States Patent
Sommers et al.

(10) Patent No.: US 11,883,039 B2
(45) Date of Patent: Jan. 30, 2024

(54) DRILL HAVING RADIOGRAPHICALLY VISIBLE DEPTH INDICATIONS

(71) Applicant: Acumed LLC, Hillsboro, OR (US)

(72) Inventors: Mark B. Sommers, Beaverton, OR (US); Scott F. Mastroianni, Forest Grove, OR (US)

(73) Assignee: Acumed LLC, Hillsboro, OR (US)

( * ) Notice: Subject to any disclaimer, the term of this patent is extended or adjusted under 35 U.S.C. 154(b) by 76 days.

(21) Appl. No.: 17/412,829

(22) Filed: Aug. 26, 2021

(65) Prior Publication Data

US 2022/0061859 A1    Mar. 3, 2022

Related U.S. Application Data

(60) Provisional application No. 63/074,099, filed on Sep. 3, 2020.

(51) Int. Cl.
*A61B 17/17*    (2006.01)
*A61B 90/00*    (2016.01)

(52) U.S. Cl.
CPC .......... *A61B 17/1703* (2013.01); *A61B 90/06* (2016.02); *A61B 90/39* (2016.02); *A61B 2090/062* (2016.02); *A61B 2090/3966* (2016.02)

(58) Field of Classification Search
CPC ..... A61B 17/1703; A61B 90/06; A61B 90/39; A61B 2090/062; A61B 2090/3966
See application file for complete search history.

(56) References Cited

U.S. PATENT DOCUMENTS

| | | | | |
|---|---|---|---|---|
| 4,005,527 A | * | 2/1977 | Wilson | G01B 3/004 606/329 |
| 5,013,318 A | * | 5/1991 | Spranza, III | A61B 17/88 33/512 |
| 5,122,146 A | * | 6/1992 | Chapman | A61B 17/1717 606/67 |

(Continued)

OTHER PUBLICATIONS

International Search Report corresponding to related International Patent Application No. PCT/US2021/047753 dated Dec. 6, 2021, 3 pages.

(Continued)

*Primary Examiner* — Kevin T Truong
*Assistant Examiner* — Diana Jones
(74) *Attorney, Agent, or Firm* — K&L Gates LLP

(57) ABSTRACT

A drill component is provided that enables determining the drill component's insertion depth into bone via direct measurements. The direct measurements help provide more consistently accurate insertion depth measurements as compared to typical insertion depth measurement methods that indirectly determine insertion depth using cannulas outside of the bone. The determined insertion depth corresponds to an implant size or length that a surgeon should select for a procedure. The drill component includes a shaft having an insertion end that includes multiple indications or markings that are visible on radiographic or fluoroscopic images. From one or more captured radiographic or fluoroscopic images of the drill component advanced into bone, a surgeon may count a quantity of indications or markings of the drill component on the one or more radiographic or fluoroscopic images to determine the drill component's insertion depth into the bone.

13 Claims, 3 Drawing Sheets

(56) References Cited

U.S. PATENT DOCUMENTS

| | | | |
|---|---|---|---|
| 8,906,094 B2* | 12/2014 | Roche | A61B 17/7097 |
| | | | 623/17.12 |
| 9,668,775 B2* | 6/2017 | Smith | A61B 17/7082 |
| 2006/0085005 A1* | 4/2006 | Kenealy, III | A61C 8/0089 |
| | | | 606/80 |
| 2007/0270864 A1 | 11/2007 | Gurtowski | |
| 2016/0022284 A1* | 1/2016 | Lele | A61B 17/17 |
| | | | 606/91 |
| 2017/0007307 A1* | 1/2017 | Cocaign | A61B 90/06 |
| 2017/0079698 A1* | 3/2017 | Fallin | A61B 17/725 |
| 2018/0008288 A1* | 1/2018 | Prescott | A61B 17/1615 |
| 2019/0083271 A1 | 3/2019 | Donner et al. | |

OTHER PUBLICATIONS

International Written Opinion corresponding to related International Patent Application No. PCT/US2021/047753 dated Dec. 6, 2021, 5 pages.

International Preliminary Report corresponding to related International Patent Application No. PCT/US2021/047753 dated Mar. 16, 2023, 8 pages.

* cited by examiner

DRILL HAVING RADIOGRAPHICALLY VISIBLE DEPTH INDICATIONS

PRIORITY CLAIM

The present application claims priority to and the benefit of U.S. Provisional Application 63/074,099, filed Sep. 3, 2020, the entirety of which is herein incorporated by reference.

BACKGROUND

Various surgical procedures involve drilling a bone hole and inserting an implantable device (e.g., screw, bushing) into the bone hole. Determining a proper length of the implantable device for the procedure involves determining an insertion depth of the drill into the bone. Typically, measurements are taken by laser markings on the drill with respect to the cannula, or laser markings on guide wires. Both of these measurement techniques are performed outside the bone, which may result in inaccurate measurements because the cannulas do not always sit flush on the bone, but rather at an angle. The reference point for the measurement therefore shifts to the most prominent contact area of the bone and the cannula, which might not necessarily result in the correct depth for the implant. Additional errors may occur when the cannula does not contact the bone surface, but rests on soft tissue instead. The cannula resting on soft tissue may lead to an increased length measurement that can result in choosing an implant that is too long.

Accordingly, a drill component and measurement method to determine an insertion depth that solves the above drawbacks is desired.

SUMMARY

The present disclosure provides a drill component that includes radiographically or fluoroscopically visible indications that may be used to determine an insertion depth of the drill component into bone. The determined insertion depth may be used to determine an implant size with a more consistent accuracy as compared to typical measurement techniques.

In an example, a method for determining an insertion depth of a drill component includes selecting a drill component having a shaft with a leading end that includes a cutting tip and a plurality of radiographically or fluoroscopically visible indications. A hole may be drilled into a bone using the selected drill component such that the drill component is advanced into the bone. An insertion depth of the drill component may be determined using a radiographic or fluoroscopic image based on the plurality of radiographically or fluoroscopically visible indications while the drill component remains advanced into the bone.

In an example, a drill component includes a shaft having an insertion end including a cutting tip and a plurality of radiographically or fluoroscopically visible indications spaced from one another. Each of the plurality of radiographically or fluoroscopically visible indications is at least one of: (1) a groove in the shaft, and (2) a first material having a higher density than a second material of which the shaft is constructed.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

DETAILED DESCRIPTION

A drill component is provided that enables determining an insertion depth of the drill component into bone with a more consistent degree of accuracy than typical insertion depth measurement methods. The determined insertion depth corresponds to an implant size or length that a surgeon should select for a procedure. The drill component includes a shaft. At one end of the shaft is an insertion end that includes a cutting tip for driving into bone to generate a bone hole. In some instances, the shaft's opposite, trailing end is configured to removably couple to a driver (e.g., a drill) or other torsion-generating device. In other instances, the shaft's opposite, trailing end may be connected to a driver or other torsion-generating device. The shaft's insertion end also includes multiple indications or markings that are radiographically or fluoroscopically visible. The multiple indications or markings do not absorb x-rays and are therefore visible in radiographic and fluoroscopic images.

A surgeon may drill a bone hole using the drill component such that its insertion end is advanced into the bone. Subsequent to or concurrently with drilling the bone hole, the surgeon may capture one or more radiographic or fluoroscopic images of the patient including the bone having the drilled hole. The image(s) are captured while the drill component remains advanced into the bone. From the one or more captured radiographic or fluoroscopic images, the surgeon may count a quantity of indications or markings on the drill component to determine the drill component's insertion depth into the bone, since the indications or markings appear on the images. For instance, the surgeon may identify where the bone's near cortex lines up relative to the indications or markings and count how many indications or markings are between the near cortex and the drill component's insertion end. The surgeon may select an implant size for the procedure based on the determined insertion depth.

The provided drill component and method therefore enable direct measurements of the drill component's insertion depth in the bone in comparison to the typical indirect measurement methods that rely upon a cannula outside of the bone, which might not always sit flush with a bone or which might rest on soft tissue. Accordingly, the provided drill component and method enable more consistently accurate insertion depth measurements. The more consistently accurate measurement of the drill component's insertion depth helps a surgeon to more consistently determine the correct or optimal implant size for a procedure as compared to typical methods, which may help lead to reduced surgical complications such as proud implants. A proud implant is an implant that protrudes too far from the bone on either of the implant's ends, which can lead to soft tissue irritation such as tendon rubbing that may eventually rupture the tendon and require a second surgery to repair the ruptured tendon.

Figure 1A:
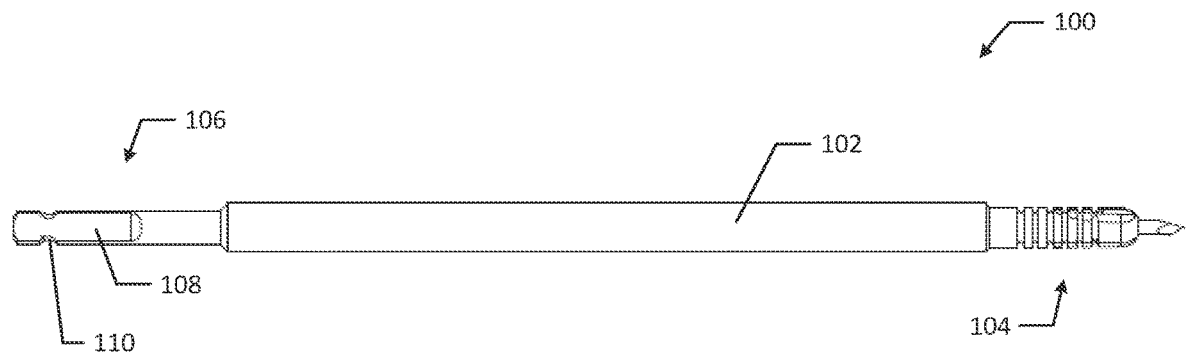
FIGS. 1A to 1C illustrate perspective views of a drill component rotated relative to one another along the drill component's long axis, according to an aspect of the present disclosure.
Figure 1B:
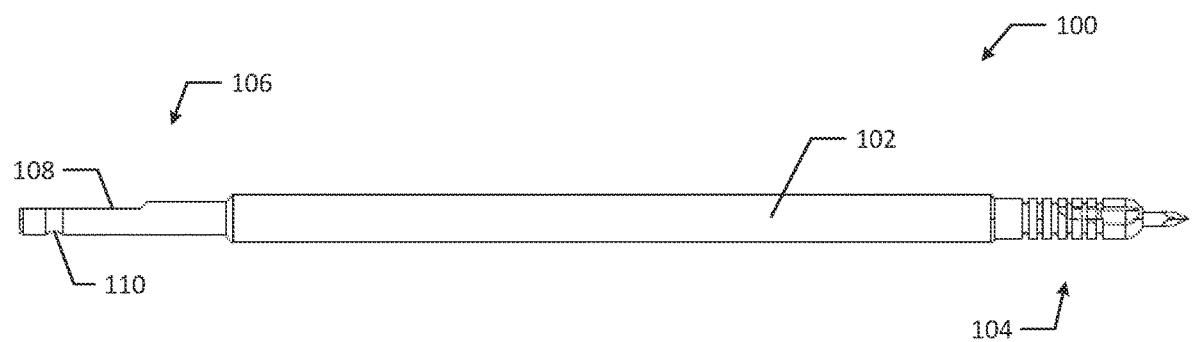
Figure 1C:
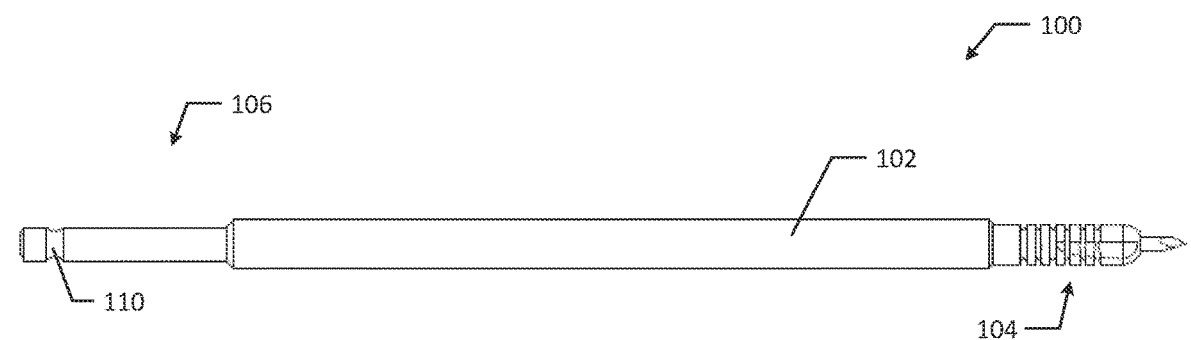

FIGS. 1A to 1C illustrate perspective views of a drill component 100 rotated relative to one another along the long axis of the drill component 100. FIG. 1B is rotated ninety degrees relative to FIG. 1A, and FIG. 1C is rotated ninety degrees relative to FIG. 1B. The drill component 100 includes a shaft 102. The shaft 102 has an insertion end 104 and a trailing end 106. In some aspects, the trailing end 106 may be configured such that the drill component 100 may be removably coupled to a driver or other torsion-generating device. For example, the trailing end 106 is constructed as an AO driver feature in FIGS. 1A to 1C having a recessed surface 108 and a groove 110 typical of an AO driver feature. In other aspects, the trailing end 106 may be connected to a driver or other torsion-generating device such that the drill component 100 is not removable. The insertion end 104 is configured to drive into bone to generate a bone hole. The insertion end 104 also includes multiple radiographically or fluoroscopically visible indications or markings.

The shaft 102 of the drill component 100 may be constructed of a suitable medical-grade material. For example, the shaft 102 may be constructed of stainless steel, a cobalt-chromium alloy, titanium, a titanium alloy, carbon fiber reinforced plastic, PEEK, polyetherimide (Ultem®), or polyoxymethylene (Delrin®).

Figure 2:
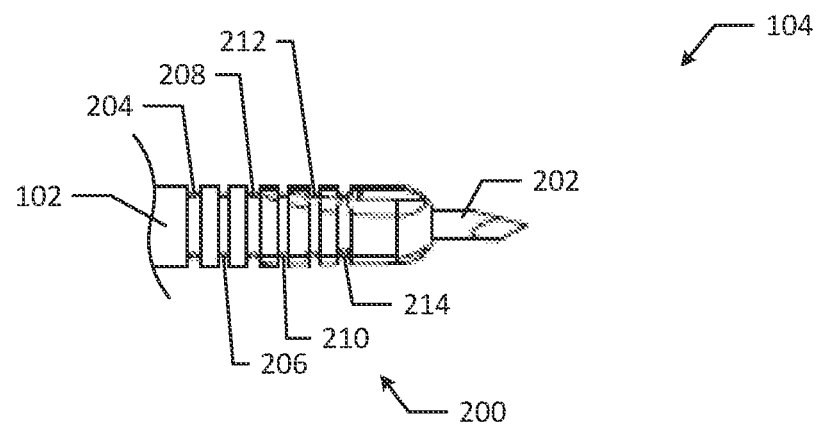
FIG. 2 illustrates a perspective view of a drill component's insertion end having grooves, according to an aspect of the present disclosure.

FIG. 2 illustrates a perspective view of an example insertion end 104 of the drill component 100. The insertion end 104 includes a cutting tip 202. The cutting tip 202 may have any suitable construction such that it enables the drill component 100 to drive into bone when the drill component 100 is driven by a driver or other torsion-generating device. The insertion end 104 also includes a plurality of indications or markings 200. In this example, the plurality of indications or markings 200 are grooves 204-214 in the shaft 102 of the drill component 100. In some instances, each of the grooves 204-214 may extend around the full perimeter of the shaft 102. In other instances, one or more of the grooves 204-214 may cover less than the full perimeter of the shaft 102.

The absence of material at each of the grooves 204-214 does not absorb x-rays while the shaft 102 does absorb x-rays. The absence of material at each of the grooves 204-214 is therefore distinguished from the shaft 102 on a radiographic or fluoroscopic image of the example insertion end 104 inserted within a patient such that a surgeon may delineate each of the grooves 204-214 on the radiographic or fluoroscopic image. In this way, the grooves 204-214 are radiographically or fluoroscopically visible. In other examples, the plurality of indications or markings 200 may be a suitable absence of material other than the grooves 204-214. For instance, the plurality of indications or markings 200 may be cross-holes that extend through the shaft 102 perpendicular to the long axis of the drill component 100. For example, each respective groove 204-214 may instead be multiple cross-holes (e.g., each cross-hole converges at a centered cavity in the shaft 102).

Figure 3:
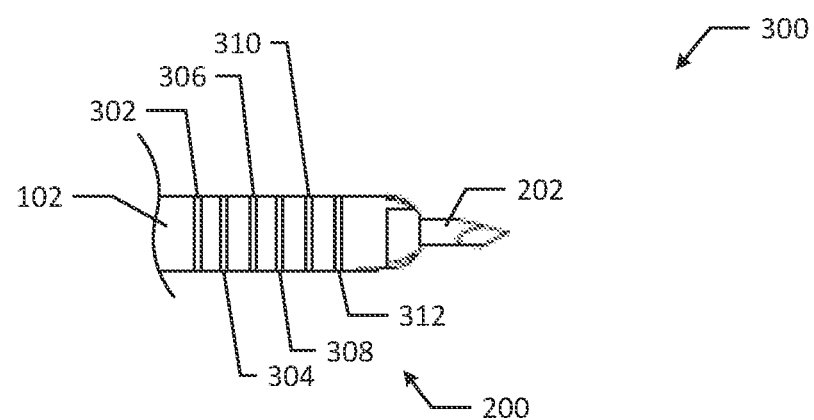
FIG. 3 illustrates a perspective view of a drill component's insertion end having markings that continuously extend around the perimeter of the drill component's shaft, according to an aspect of the present disclosure.

In an alternative example, the plurality of indications or markings 200 may instead be provided by a material having a different density than the shaft 102. FIG. 3 illustrates a perspective view of an example insertion end 300 of the drill component 100 in which the plurality of indications or markings 200 are the markings 302-312. The markings 302-312 may be printed on the shaft 102. The markings 302-312 are constructed of a material having a higher density than the material from which the shaft 102 is constructed. For example, the markings 302-312 may be constructed from a radiopaque ink (e.g., an ink including barium, silver, etc.), or other suitable medical-grade material based on the material of the shaft 102 in a particular aspect of the present disclosure. The higher-density material of the markings 302-312 absorbs more x-rays than the lower-density material of the shaft 102. The markings 302-312 are therefore distinguished from the shaft 102 on a radiographic or fluoroscopic image of the example insertion end 300 inserted within a patient such that a surgeon may delineate each of the markings 302-312 on the radiographic or fluoroscopic image. In this way, the markings 302-312 are radiographically or fluoroscopically visible.

Figure 4:
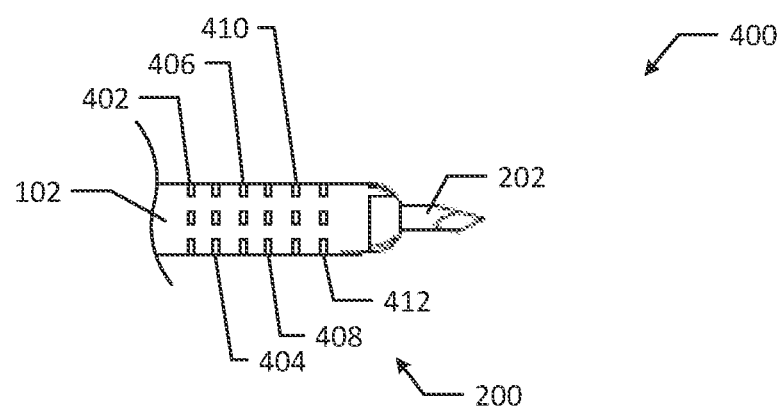
FIG. 4 illustrates a perspective view of a drill component's insertion end having markings that extend a portion around the perimeter of the drill component's shaft, according to an aspect of the present disclosure.

As with the grooves 204-214, the markings 302-312 may continuously extend around the perimeter of the shaft 102 or may extend a portion less than the entire perimeter. FIG. 4 illustrates a perspective view of an insertion end 400 having example markings 402-412 that extend a portion less than the entire perimeter of the shaft 102. The markings 402-412 of the insertion end 400 are dots or dashed markings. It should be appreciated that each of the markings 402-412 may be in any suitable shape or form such that they delineate separate markings along the shaft 102.

In some aspects of the present disclosure, the drill component 100 may have an insertion end with a plurality of indications or markings 200 that combines any of the features of the example insertion ends 104, 300, and 400. For example, the drill component 100 may have the insertion end 104 including the grooves 204-214 and also including markings 302-312 on the inner diameter of the shaft 102 at each of the grooves 204-214. In another example, the plurality of indications or markings 200 may alternate between a groove and a marking. For instance, with reference to the insertion end 104, the grooves 206, 210, and 214 of the insertion end 104 may instead be the markings 304, 308, and 312. In another instance, with reference to the insertion end 300, the markings 302, 306, 310 of the insertion end 300 may instead be the markings 302, 306, 310 of the insertion end 400.

The plurality of indications or markings 200 may include any suitable quantity (e.g., four, five, six, seven, etc.) of individual indications or markings. For instance, the example insertion ends 104, 300, and 400 include six individual indications or markings. Each of the plurality of indications or markings 200 may be equally spaced apart from one another. In some aspects, at least some of the plurality of indications or markings 200 are unequally spaced apart from one another.

Figure 5:
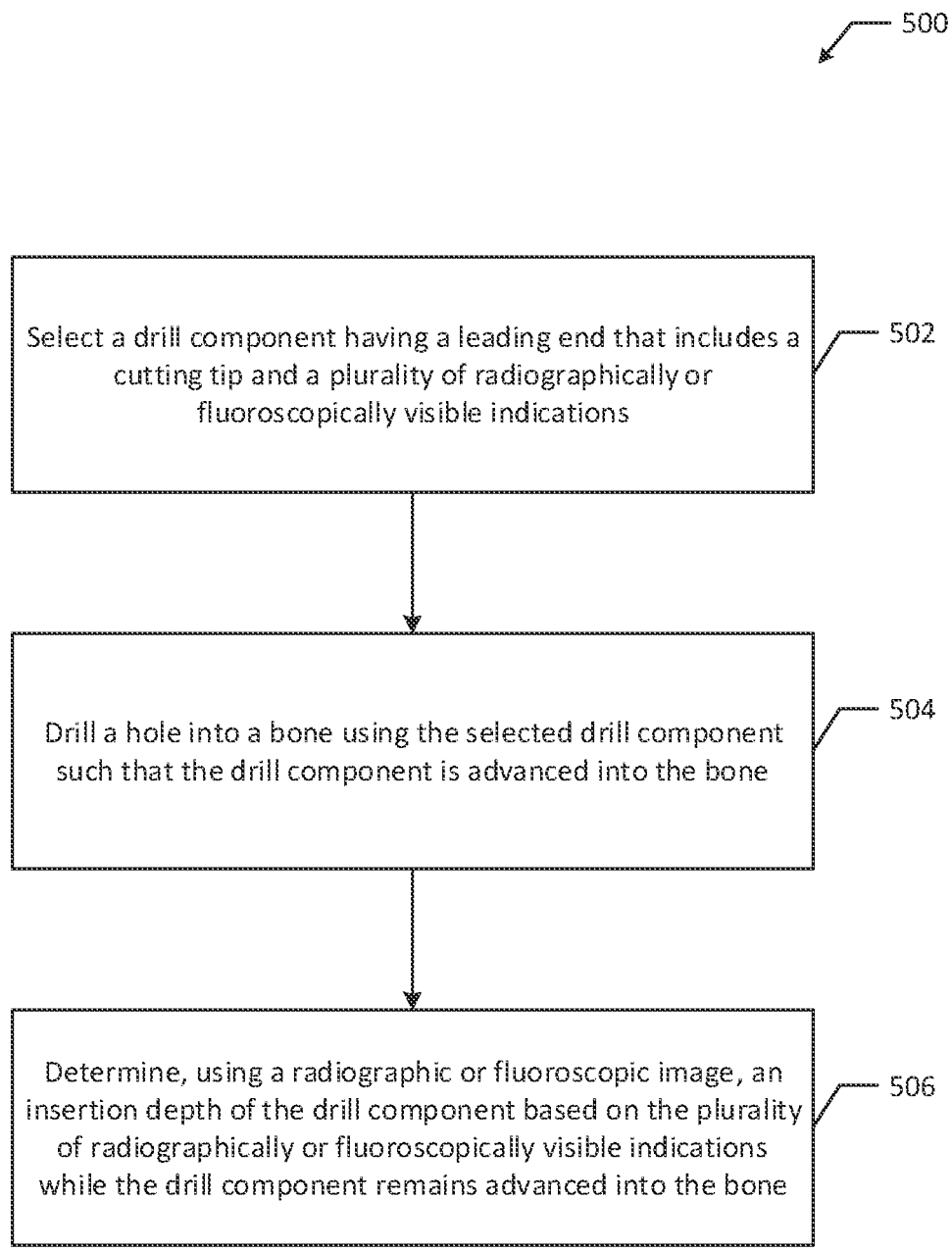
FIG. 5 illustrates a flow chart of an example method for determining an insertion depth of a drill component, according to an aspect of the present disclosure.

FIG. 5 shows a flow chart of an example method 500 for determining an insertion depth of a drill component. Although the example method 500 is described with reference to the flowchart illustrated in FIG. 5, it will be appreciated that many other methods of performing the acts associated with the method 500 may be used. For example, the order of some of the blocks may be changed, certain blocks may be combined with other blocks, and some of the blocks described are optional.

In the example method 500, a drill component may be selected having a leading end that includes a cutting tip and a plurality of radiographically or fluoroscopically visible indications (block 502). For example, the drill component 100 described above may be selected. A hole may be drilled into a bone using the selected drill component such that the drill component is advanced into the bone (block 504). In some aspects, fluoroscopic images of the bone may be continuously captured while the hole is drilled into bone so that a surgeon may see real-time moving images of the drill component 100 advancing into the bone. In other aspects, fluoroscopic or radiographic image(s) of the bone may be periodically captured so that the surgeon may check a positioning of the drill component 100 in the bone.

Using a radiographic or fluoroscopic image, an insertion depth of the drill component is determined based on the plurality of radiographically or fluoroscopically visible indications while the drill component remains advanced into the bone (block 506). In some instances, the hole may be drilled to a desired depth, and then the insertion depth of the drill component 100 may be determined. In other instances, the hole may be drilled until it is determined, using the radiographic or fluoroscopic image, that the drill component 100 has reached a specific landmark (e.g., contacting the far cortex) or that the drill component 100 is otherwise at a desired insertion depth.

As described above, the plurality of indications or markings 200 on the drill component 100 appear on a radiographic or fluoroscopic image. A surgeon may therefore determine an insertion depth of the drill component 100 by counting a quantity of individual indications or markings of the plurality of indications or markings 200. For instance, the surgeon may identify, on the radiographic or fluoroscopic image, where the bone's near cortex lines up relative to the indications or markings and count how many indications or markings are between the near cortex and the insertion end of the drill component 100. Each of the plurality of markings 200 may be spaced a certain distance apart (e.g., 2 mm) and thus counting a quantity of indications or markings enables the surgeon to determine a depth measurement. In some instances, the bone's near cortex may line up between two indications or markings and the surgeon may estimate a value between the two indications or markings.

A size of an implant (e.g., a screw, bushing, etc.) may be selected for a procedure based on the determined insertion depth of the drill component 100. In some aspects, each of the plurality of indications or markings 200 corresponds to a particular insertion depth (e.g., 6 mm, 8 mm, 10 mm, etc.) of the drill component 100. In such aspects, an implant size may be selected using the particular insertion depth that is determined. In other aspects, each of the plurality of markings 200 corresponds to a particular implant size. In such other aspects, determining an insertion depth of the drill component 100 also determines an implant size for selection.

Accordingly, the example method 500 enables a surgeon to determine an insertion depth of the drill component 100, and an implant size for a procedure, by taking a direct measurement of the drill component 100 within the bone using a radiographic or fluoroscopic image. The direct measurements of the method 500 help increase the consistency of accurate depth measurements as compared to typical indirect measurement methods that utilize cannulas outside of the bone.

As used herein and in the appended claims, the singular form of a word includes the plural, unless the context clearly dictates otherwise. Thus, the references "a," "an" and "the" are generally inclusive of the plurals of the respective terms. For example, reference to "an indication" or "a marking" includes a plurality of such "indications" or "markings." The term "and/or" used in the context of "X and/or Y" should be interpreted as "X," or "Y," or "X and Y."

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A method for determining an insertion depth of a drill component comprising:
   selecting a drill component having a shaft with a leading end that includes a cutting tip and a plurality of radiographically or fluoroscopically visible indications;
   drilling a hole into a bone using the selected drill component such that the drill component is advanced into the bone; and
   determining, using a radiographic or fluoroscopic image, an insertion depth of the drill component based on the plurality of radiographically or fluoroscopically visible indications while the drill component remains advanced into the bone.

2. The method of claim 1, wherein determining the insertion depth of the drill component includes identifying a location on the shaft at which a near cortex, corresponding to the bone, lines up and counting a quantity of radiographically or fluoroscopically visible indications that are between the cutting tip and the location on the shaft.

3. The method of claim 1, wherein the hole is drilled into the bone to a desired depth prior to determining the insertion depth of the drill component.

4. The method of claim 1, further comprising observing fluoroscopic images continuously generated while drilling the hole into the bone.

5. The method of claim 4, wherein advancing the drill component into the bone to drill the hole is terminated upon determining an insertion depth that is a desired insertion depth.

6. The method of claim 1, wherein each of the plurality of radiographically or fluoroscopically visible indications corresponds to a length measurement.

7. The method of claim 1, wherein each of the plurality of radiographically or fluoroscopically visible indications corresponds to an implant size.

8. The method of claim 1, further comprising selecting an implant size based on the determined insertion depth of the drill component.

9. The method of claim 1, wherein each of the plurality of radiographically or fluoroscopically visible indications is a groove in the drill component.

10. The method of claim 9, wherein one or more of the respective grooves extends around an entire perimeter of the drill component.

11. The method of claim 1, wherein the drill component is constructed of a first material having a first density, and wherein each of the plurality of radiographically or fluoroscopically visible indications is constructed of a second material having a second density that is greater than the first density.

12. The method of claim 11, wherein the second material is a radiopaque ink.

13. The method of claim 1, wherein the plurality of radiographically or fluoroscopically visible indications are equally spaced apart from one another.

* * * * *